US012623020B2

(12) United States Patent (10) Patent No.: US 12,623,020 B2
Yang (45) Date of Patent: May 12, 2026

(54) ANALYTE DETECTION SYSTEM AND CONTINUOUS GLUCOSE MONITORING DEVICE

(71) Applicant: MEDTRUM TECHNOLOGIES INC., Shanghai (CN)

(72) Inventor: Cuijun Yang, Shanghai (CN)

(73) Assignee: MEDTRUN TECHNOLOGIES INC., Shanghai (CN)

( * ) Notice: Subject to any disclaimer, the term of this patent is extended or adjusted under 35 U.S.C. 154(b) by 405 days.

(21) Appl. No.: 18/035,112

(22) PCT Filed: Jul. 8, 2021

(86) PCT No.: PCT/CN2021/105101
§ 371 (c)(1),
(2) Date: May 3, 2023

(87) PCT Pub. No.: WO2022/116539
PCT Pub. Date: Jun. 9, 2022

(65) Prior Publication Data
US 2024/0000398 A1 Jan. 4, 2024

(30) Foreign Application Priority Data

Dec. 4, 2020 (WO) ................ PCT/CN2020/133734

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14503* (2013.01); *A61B 5/14532* (2013.01);
(Continued)

(58) Field of Classification Search
CPC .............. A61B 5/14532; A61B 5/7475; A61B 2562/0219; A61M 5/14248
See application file for complete search history.

(56) References Cited

U.S. PATENT DOCUMENTS

2015/0057770 A1* 2/2015 Bailey ................... A61B 5/389
700/83
2015/0173674 A1* 6/2015 Hayes ................... G16H 40/67
600/300
(Continued)

FOREIGN PATENT DOCUMENTS

CN 102576375 7/2012
CN 203576512 5/2014
(Continued)

OTHER PUBLICATIONS

"International Search Report (Form PCT/ISA/210) of PCT/CN2021/105101," mailed on Oct. 11, 2021, pp. 1-2.

*Primary Examiner* — Christian Jang
(74) *Attorney, Agent, or Firm* — JCIP GLOBAL INC.

(57) ABSTRACT

An analyte detection system, includes a bottom case housing, which is used for mounting to the surface of human skin; a sensor mounted on the bottom case housing for detecting the analyte parameter information; a transmitter unit including a transmitters shell, an internal circuit, a transmitter and a motion sensor, the transmitter sending the analyte parameter information to the outside world, the motion sensor connected to the internal circuit operationally, used for induction or identify the user's body movements. According to induction or recognition of body movements by the motion sensor, the internal circuit controls the sensor or the transmitter to execute the corresponding functional instructions to enhance the user experience.

14 Claims, 5 Drawing Sheets

(51) Int. Cl.

| | |
|---|---|
| *A61B 5/145* | (2006.01) |
| *A61M 5/14* | (2006.01) |
| *A61M 5/142* | (2006.01) |
| *A61M 5/145* | (2006.01) |
| *A61M 5/168* | (2006.01) |
| *G16H 20/17* | (2018.01) |

(52) U.S. Cl.

CPC ............ *A61B 5/746* (2013.01); *A61B 5/7475* (2013.01); *A61M 5/14* (2013.01); *A61M 5/142* (2013.01); *A61M 5/14248* (2013.01); *A61M 5/1452* (2013.01); *A61M 5/16804* (2013.01); *A61M 5/16831* (2013.01); *G16H 20/17* (2018.01); *A61B 2562/0219* (2013.01); *A61M 2005/14208* (2013.01); *A61M 2205/103* (2013.01); *A61M 2205/276* (2013.01); *A61M 2205/33* (2013.01); *A61M 2209/01* (2013.01); *A61M 2230/201* (2013.01)

(56) References Cited

U.S. PATENT DOCUMENTS

| | | |
|---|---|---|
| 2016/0354543 A1 | 12/2016 | Cinar et al. |
| 2017/0290534 A1 * | 10/2017 | Antonio ............... A61B 5/6832 |

FOREIGN PATENT DOCUMENTS

| | | |
|---|---|---|
| WO | 2018058287 | 4/2018 |
| WO | 2018120104 | 7/2018 |
| WO | 2019213608 | 11/2019 |
| WO | 2021031542 | 2/2021 |

* cited by examiner

ANALYTE DETECTION SYSTEM AND CONTINUOUS GLUCOSE MONITORING DEVICE

CROSS-REFERENCE TO RELATED APPLICATION

This application is a 371 of international application of PCT application serial no. PCT/CN2021/105101, filed on Jul. 8, 2021, which claims the priority benefit of PCT application no. PCT/CN2020/133734, filed on Dec. 4, 2020. The entirety of each of the above-mentioned patent applications is hereby incorporated by reference herein and made a part of this specification.

TECHNICAL FIELD

The invention mainly relates to the field of medical devices, in particular to an analyte detection system.

BACKGROUND

The pancreas in a normal human body can automatically monitor the blood glucose level and automatically secrete required amount of insulin/glucagon. In the body of a type 1 diabetes patient, the pancreas does not function properly and cannot produce enough insulin for the body. Therefore, type 1 diabetes is a metabolic disease caused by abnormal pancreatic function, and diabetes is a lifelong disease. At present, there is no cure for diabetes with medical technology. The onset and development of diabetes and its complications can only be controlled by stabilizing blood glucose.

Diabetics need to have their blood glucose measured before they inject insulin into the body. At present, most of the testing methods can continuously measure blood glucose level and send the data to a remote device in real time for the user to view. This method is called Continuous Glucose Monitoring (CGM). The method requires the device to be attached to the skin and the sensor in the device is inserted into the subcutaneous tissue fluid.

At present, when using the analyte detection system, users need to locate different input positions in the remote device and manually input instructions on the remote device, so as to control the analyte detection system to perform the corresponding functions. This input process is cumbersome and the user experience is poor.

Therefore, the existing technology is in urgent need of an analyte detection system that simplifies the instruction input process and provides better user experience.

BRIEF SUMMARY OF THE INVENTION

The invention discloses an analyte detection system. After the user's body movement is sensed or recognized by a motion sensor as an instruction, the internal circuit can directly control the sensor or transmitter to execute the instruction, without the user manually entering the instruction on the remote device, thus improving the user's experience.

The invention discloses an analyte detection system, which comprises a bottom case housing, which is used for mounting to the surface of human skin. The sensor comprises an analyte detection sensor and a conductive tape. The analyte detection sensor is inserted under the human skin to detect the parameter information of the analyte. The conductive tape consists of conductive areas and insulating areas, which are arranged alternately. The transmitter unit comprises a transmitter housing, an internal circuit, a transmitter and a motion sensor. The internal circuit is arranged in the transmitter housing, and the internal circuit includes at least a first electrical contact leading to the outside of the transmitter housing. The first electrical contact is in electric contact with the conductive tape to obtain the parameter information of the analyte. The transmitter is used to send the parameter information of the analyte to the outside world. The motion sensor is operationally connected with the internal circuit for sensing or recognizing the user's body movements. Once the motion sensor senses or recognizes the body movements, the internal circuit controls the sensor unit or transmitter to execute the corresponding instructions. And A battery is included in the transmitter unit as power source.

According to one aspect of the invention, the battery is sealed inside the transmitter housing to provide electrical energy to the transmitter unit.

According to one aspect of the invention, the battery is embedded in the bottom case housing which includes at least two second electrical contacts, respectively connected to the cathode and anode, the internal circuit includes third electrical contacts which lead to the outside of the transmitter housing and correspond to the second electrical contacts, the third electrical contacts are electrically connected to the second electrical contacts, allowing the battery to power the transmitter unit. According to one aspect of the invention, the inner circuit also includes a first subcircuit connected to the sensor and a second subcircuit connected to the transmitter, and the first subcircuit and the second subcircuit are electrically connected.

According to one aspect of the invention the motion sensor is respectively connected to a first subcircuit and a second subcircuit.

According to one aspect of the present invention, a motion sensor comprises a first sub-motion sensor and a second sub-motion sensor, wherein the first subcircuit is electrically connected to the first sub-motion sensor, the second subcircuit is electrically connected to the second sub-motion sensor, and the first subcircuit is electrically connected to the second subcircuit.

According to one aspect of the invention, the instructions include sensor calibration, sensor activation or stop, adjustment of the alarm threshold of blood glucose levels, on/off alarm, adjustment of signal strength, on/off signal transmission, connection/disconnection of remote device, switching of user's body state, event start and event end.

According to one aspect of the invention, the body movements include walking, jumping, running, squatting, leg movements, arm movements, bending, body twisting and/or flapping, swinging and pressing of the motion sensor.

According to one aspect of the invention, an internal circuit controls the sensor unit or transmitter to execute the instructions corresponding to a certain number and/or combination of body movements.

According to one aspect of the invention, the body movements sensed or recognized within a fixed time period t by the motion sensor are recognized as effective movements while the body movements sensed or recognized beyond the fixed time period t are recognized as ineffective movements. Only effective movements can send instructions to the inner circuit which then controls the sensor unit or transmitter to execute the instructions. According to one aspect of the invention, the fixed time period t is between 0.5 second and 5 seconds.

According to one aspect of the invention, the fixed time period t=1 second.

According to one aspect of the invention, a motion sensor includes one or more of an acceleration sensor, an inclination sensor, a vibration sensor and a rotation sensor.

According to one aspect of the invention, the acceleration sensor is a three-axis acceleration sensor.

According to one aspect of the invention, a body movement confirmation module is also included, which is connected with a motion sensor and is used to instruct the motion sensor to begin/end sensing or recognizing the user's body movements.

According to one aspect of the invention, a continuous glucose monitoring device is also disclosed, comprising an analyte detection system and a receiver for receiving analyte parameter information transmitted by a transmitter and showing the analyte parameter information to the user.

Compared with the prior art, the technical scheme of the invention has the following advantages:

In the analyte detection system disclosed in the invention, the motion sensor is used to sense or recognize the user's body movements, and different body movements send different instructions. According to the body movements sensed or recognized by the motion sensor, the internal circuit controls the sensor or transmitter to execute the corresponding instructions. Compared with manual input, the direct use of body movements as instructions doesn't require the user to look for the instruction input locations on the remote device which is simpler and more convenient, and provides better user experience.

Further, the battery is sealed inside the transmitter housing, which has a good is waterproof rating and allows users to carry out underwater sports, thus providing better user experience.

Further, the battery is embedded in the bottom case housing. As the bottom case housing is disposable, the user will replace the battery every time replacing the bottom case housing, so the analyte detection system can maintain the high performance of battery, thus providing reliable detection data.

Further, body movements include walking, jumping, running, squatting, leg movements, arm movements, bending, torso twisting and/or flapping, swinging and pressing of the motion sensor. There are many kinds of body movements and they are relatively easy to be performed by users.

Further, the combination of different numbers and types of body movements also improves the flexibility and safety of the analyte detection system in executing instructions.

Further, the body movements sensed or recognized within a fixed time period t by the motion sensor are recognized as effective movements. The internal circuit controls the sensor unit or transmitter to execute instructions based on the effective movements, which prevents the execution of false instructions from excess body movements of users, and improves the security of the system.

Further, the analyte detection system also includes a body movement confirmation module, which is connected with a motion sensor. The body movement confirmation module is used to confirm whether the user's body movements meet the standards or requirements, which improves the security of the analyte detection system.

Further, the motion sensor includes one or more of the acceleration sensor, tilt sensor, vibration sensor and rotation sensor. A variety of motion sensors can be selected and combined to improve the accuracy and sensitivity of identifying body movements.

Further, the acceleration sensor is a three-axis acceleration sensor. The three-axis acceleration sensor can detect the change of acceleration in X, Y and Z axes, with the advantage of rapid detection of body movements, improving the sensitivity of movement detection.

Further, the internal circuit comprises a first subcircuit connected with the sensor and a second subcircuit connected with the transmitter, the first subcircuit and the second subcircuit are electrically connected, the motion sensor is respectively connected with the first subcircuit and the second subcircuit. When a body movement corresponding to a sensor-related instruction is sensed by the motion sensor, a signal will be generated, which will only be received by the first subcircuit instead of the second subcircuit. When a body movement corresponding to a transmitter-related instruction is sensed by the motion sensor, a signal will be generated, which will only be received by the second subcircuit instead of the first subcircuit, thus improving the accuracy of motion detection.

Further, the motion sensor includes a first sub-motion sensor and a second sub-motion sensor, the first subcircuit is electrically connected with the first sub-motion sensor, the second subcircuit is electrically connected with the second sub-motion sensor, and the first subcircuit is electrically connected with the second subcircuit. The first sub-motion sensor stores the body movement data corresponding to the sensor-related instructions, and the second sub-motion sensor stores the body movement data corresponding to the transmitter-related instructions. When the user performs a body movement corresponding to a sensor-related instruction, the first sub-motion sensor can recognize it and generate a signal, which is transmitted to the first subcircuit. The first subcircuit controls the sensor to execute the corresponding instruction, while the second sub-motion sensor cannot recognize the body movement at this time. Thus, the design improves the accuracy of motion detection and yet reduces the power consumption of the system.

The present invention also made public a continuous glucose monitoring device, including an analyte detection system and a receiver for receiving the analyte parameter information sent by the transmitter, and showing analyte parameter information to the user; the analyte detection system includes a body-movement-instruction detection system which makes the continuous glucose monitoring device simpler and more convenient, and provides better user experience.

DETAILED DESCRIPTION

As mentioned above, the prior art analyte detection system requires the user to find the instruction input location on the remote device and manually enter the instructions, resulting in poor user experience.

It is found that the reason for the above problems is that there is no sensor to sense the user's body movements in the analyte detection system, and the user's body movements cannot be used as instructions.

In order to solve this problem, the invention provides an analyte detection system, which is provided with a motion sensor for sensing or recognizing the body movements directly as instructions, thus improving the user experience.

Various exemplary embodiments of the invention will now be described in detail with reference to the attached drawings. It is understood that, unless otherwise specified, the relative arrangement of parts and steps, numerical expressions and values described in these embodiments shall not be construed as limitations on the scope of the present invention.

In addition, it should be understood that the dimensions of the various components shown in the attached drawings are not necessarily drawn to actual proportions for ease of description, e. g. the thickness, width, length or distance of some elements may be enlarged relative to other structures.

The following descriptions of exemplary embodiments are illustrative only and do not in any sense limit the invention, its application or use. Techniques, methods and devices known to ordinary technicians in the relevant field may not be discussed in detail here, but to the extent applicable, they shall be considered as part of this manual.

It should be noted that similar labels and letters indicate similar items in the appending drawings below, so that once an item is defined or described in one of the appending drawings, there is no need to discuss it further in the subsequent appending drawings.

Figure 1:
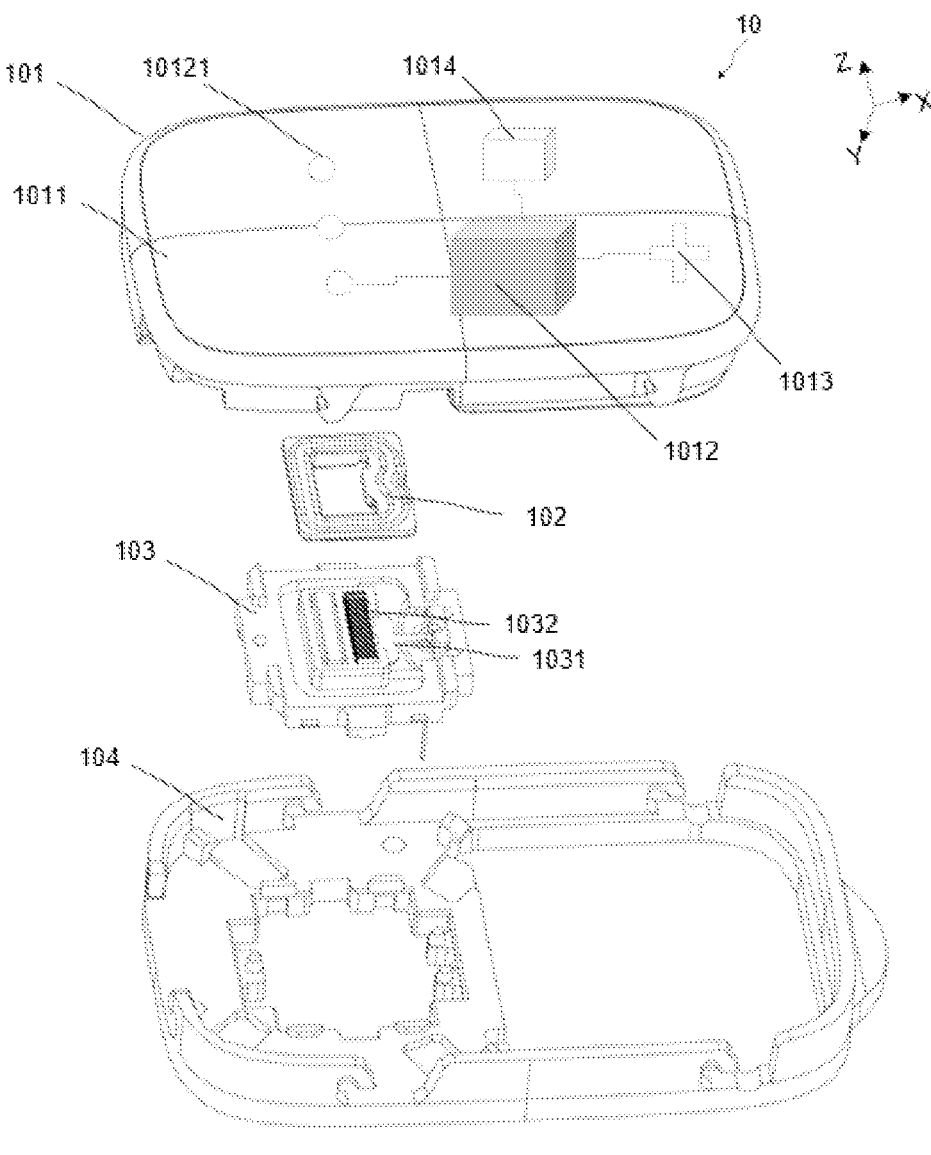
FIG. 1 is a structural schematic diagram of an analyte detection system according to an embodiment of the invention.

FIG. 1 is a structural schematic diagram of an analyte detection system according to an embodiment of the invention. The analyte detection system 10 comprises an transmitter unit 101, which comprises a transmitter housing 1011, an internal circuit 1012, an transmitter 1013 and a motion sensor 1014. The internal circuit 1012, transmitter 1013 and motion sensor 1014 are arranged inside the transmitter housing 1011.

In the embodiment of the invention, the internal circuit 1012 includes the first electric contact 10121 leading to the outer part of the transmitter housing 1011, and the area in contact with the first electric contact 10121 and the transmitter housing 1011 is laid with waterproof and insulating materials, preferably including but not limited to one or more combinations of flexible materials, elastic materials and malleable materials. Further preferred, including but not limited to one or more combinations of epoxy resins, silicone resins, and gels.

In the embodiment of the invention, the transmitter 1013 is used to transmit information to the outside world, which includes but is not limited to one or more combinations of Bluetooth, NFC, RFID, Li-Fi and WIFI. The information receiver can be users' Personal Diabetes Manager (PDM) or compatible smart devices like smart phone, tablet, etc., so that users can see the parameter information of the analyte in a visual form, which is convenient for users to use.

In the embodiment of the invention, the motion sensor 1014 includes but is not limited to one or more of the acceleration sensor, tilt sensor, vibration sensor and rotation sensor.

In one embodiment of the invention, the motion sensor 1014 is a three-axis acceleration sensor, which can detect the change of acceleration in X, Y and Z axis directions, and has the advantage of rapid detection of body movements, more comprehensive recognition of body movements, and improved sensitivity of movement detection.

In another embodiment of the invention, the motion sensor 1014 is a rotation sensor, which can accurately detect the user's body rotation movements, such as turning around, etc.

In another embodiment of the invention, the motion sensor 1014 is a vibration sensor which can accurately detect the user's flapping and other body movements.

In another embodiment of the invention, the motion sensor 1014 is a combination of a three-axis acceleration sensor, a rotation sensor and a vibration sensor. The combined motion sensor can realize even more accurate detection of body movements, give the user more choices and improve the user experience.

Continuing with FIG. 1, the analyte detection system 10 also includes a sealing ring 102 to provide waterproof protection in wet or underwater environments; The sensor 103 includes an analyte sensor 1031 and a conductive strip 1032, the analyte sensor 1031 and the conductive adhesive strip 1032 connected to each other. 2. The analyte sensor 1031 is inserted under the human skin to detect the parameter information of analytes. It is understood by technicians in this field that the analytes here include but are not limited to blood glucose. They can also be other chemicals that exist in human body fluids including blood protein, dopamine, epinephrine, thyroid hormones, etc. When the analyte(s) in the human body fluids are detected by the analyte sensor 1031, different chemical reactions will happen on the electrodes (not shown in the figure) on the analyte sensor 1031 and the membrane system (not shown in the figure) according to the species and concentrations of analyte, thus generating different forms of electrical signals, the electrical signal can be used to analyze the analyte parameter information; with the conductive adhesive strip 1032 and the first electric contact 10121 electrically connected to each other, the electrical signal generated on the analyte sensor 1031 is transmitted to the internal circuit 1012 through the conductive adhesive strip 1032 and the first electric contact 10121. After signal processing such as denoising, amplification and waveform sorting, etc., the transmitter 1013 transmits the parameter information of the analyte to the outside world, that is, the transmitter 1013 is electrically connected with the internal circuit 1012; The bottom case housing 104 is used for assembling the transmitter unit 101, sealing ring 102 and sensor 103 and is fixed on the surface of the human skin; The battery (not shown in the figure) is sealed in the transmitter unit 101 and is used to provide power to the transmitter unit 101. Since the battery is sealed in the transmitter unit 101, the transmitter unit 101 can be used in wet or underwater environments, enhancing the user experience.

Figure 2:
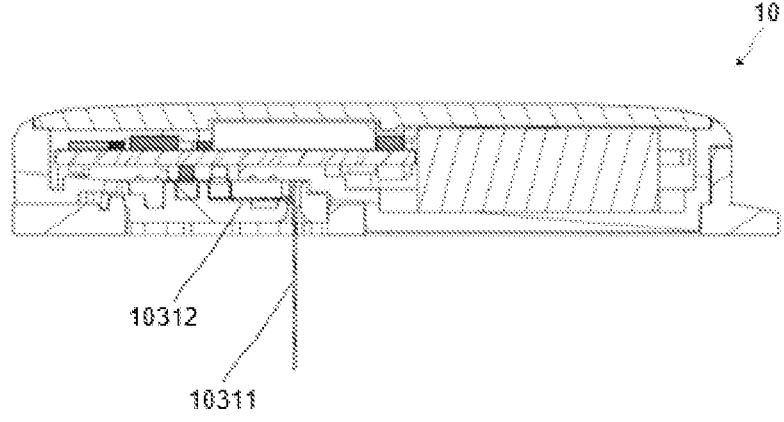
FIG. 2 is a schematic diagram of the section structure of the analyte detection system according to an embodiment of the invention.

Combined with FIG. 2, FIG. 2 is a schematic diagram of the section structure of the analyte detection system according to an embodiment of the invention.

The analyte sensor 1031 includes an internal part 10311 and an external part 10312. The internal part 10311 includes at least a working electrode, a reference electrode (not shown in figure) and a membrane system (not shown in figure). In the embodiment of the invention, the detected analyte is glucose, the working electrode and the membrane surface are equipped with glucose oxidase, glucose in human body fluids can produce hydrogen peroxide $H_2O_2$ and electrons through chemical reaction catalyzed by glucose oxidase, glucose of different concentrations produces different quantities of electrons in a given period, thus generating a current of changing intensity, which leads to different electrical signals used to indicate analyte parameter information. The external part 10312 is bent toward the surface of sensor 103, and the bending angle α is formed relative to the internal part 10311. Preferably, the bending angle α is 90°. The external part 10312 has a planar structure and is electrically contacted with the conductive adhesive strip 1032 to conduct the electrons generated by the internal part 10311 to the conductive adhesive strip 1032.

In the embodiment of the invention, the conductive adhesive strip 1032 is vulcanized and formed by alternately layered superposition of the conductive silica gel and the insulating silica gel, that is, the conductive adhesive strip 1032 exists a conductive zone and an insulating zone. One side of the conductive adhesive strip 1032 is electrically in contact with the external part 10312, and the other side is electrically in contact with the first electrical contact 10121. In this way, the electrical signal indicating the parameter information of the analyte can be transmitted to the internal circuit 1012 through the conductive area of the conductive silica gel. On the other hand, the electrical signals obtained by different electrodes can be insulated from each other and transmitted to different first electrical contacts. In other references, the conductive adhesive strip 1032 is also known as "zebra strip". It has stable and reliable performance, simple and efficient production and assembly. The conductive area has good conductive performance, while the insulating area also has good insulating performance.

With reference to FIG. 1 and FIG. 2, when the bottom case housing 104 is fixed on the user's skin surface and the internal part 10311 is punctured under the skin, the analyte detection system 10 is in the working state. In working condition, the user can set the analyte detection time interval, the types of analyte detection and analyte concentration alarm threshold, the parameters such as the field technicians can understand is that the user can operation function should not be confined to the above content, can also contain other functions for user operation, in order to enhance the user experience, for example, users can calibrate the sensor, activate or stop the sensor, turn on or remove the alarm, connect or disconnect the remote device, switch the user's body state, start and end the event, etc.

Figure 3:
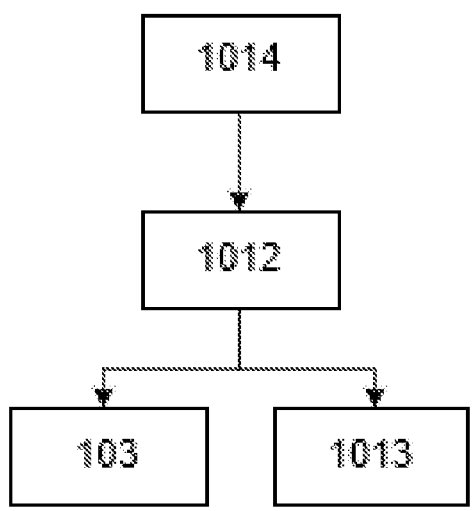
FIG. 3 is a functional schematic diagram of the motion sensor and the internal circuit.

FIG. 3 is a functional schematic diagram of the motion sensor and the internal circuit.

The motion sensor 1014 is operationally connected to the internal circuit 1012 to facilitate the transfer of instruction signals between the two. Here, "operationally connected" means that the internal circuit 1012 can directly obtain the body movement information from the motion sensor 1014, or indirectly obtain the user's body movement information from the motion sensor 1014, and control the sensor 103 or the transmitter 1013 to execute the corresponding functional instructions.

Preferably, in the embodiment of the invention, the motion sensor 1014 is electrically connected with the internal circuit 1012. The electric connection between the two is not only convenient for structural design, but also can reduce power consumption.

As described above, sensor 103 and transmitter 1013 are electrically connected to internal circuit 1012 respectively. The internal circuit 1012 is divided into the first subcircuit 10121 connected with the sensor 103 and the second subcircuit 10122 connected with the transmitter 1013. The first subcircuit 10121 and the second subcircuit 10122 can operate independently or interactively. Therefore, the internal circuit 1012 can control the sensor 103 and the transmitter 1013 respectively or simultaneously to execute the corresponding functional instructions.

In other embodiments of the present invention, sensor 103 and transmitter 1013 are respectively wirelessly connected to the internal circuit 1012, that is, sensor 103 is wirelessly connected to the first subcircuit 10121, transmitter 1013 is wirelessly connected to the second subcircuit 10122, and the first subcircuit 10121 and the second subcircuit 10122 can operate independently. It can also operate interactively, so the internal circuit 1012 can control sensor 103 and transmitter 1013 to execute the corresponding functional instructions separately or simultaneously.

In embodiments of the invention, functional instructions include functions that can be performed by sensor 103, such as including but not limited to sensor calibration, sensor activation or stop, adjustment of alarm threshold of blood glucose concentration. It also includes functions that the transmitter 1013 can perform, including but not limited to adjusting signal strength, turning on/off signal transmission, and connecting/disconnecting remote devices. It also includes functions that can be performed by both sensor 103 and transmitter 1013, including but not limited to switching the user's physical state, event start and event end.

It is important to note that the blood glucose threshold is used to alert the user when blood glucose is too high or too low. Connecting or disconnecting the remote device means that the user can choose whether to connect the sensor 103 or transmitter 1013 to the remote device according to the actual needs. Switching the user's body state means that the user switches from sitting state to sleeping state, or from sleeping state to waking state, etc. Events begin to represent the user's eating event, exercise event, or bath event, etc.

The function of the analyte detection system controlled by body movements in the embodiment of the invention is controlled by the body movements of the user. Therefore, in the embodiment of the invention, different body movements of the user represent different functional instructions.

In the embodiment of the invention, the body movements include walking, jumping, running, squatting, leg movements, arm movements, bending, body twisting or/and flapping, swinging and pressing of the motion sensor 1014 or a combination of various movements. Compared to manual input, the body movement is easier to implement and the user experience is better.

It needs to be explained here that the flapping, swinging and pressing of the motion sensor 1014 not only includes direct contact with the motion sensor 1014, but also includes indirect contact or no contact. For example, users can flap, swing and pressing the motion sensor 1014 across the clothing. Leg movements include but are not limited to leg lifting and shaking. Arm movements include but are not limited to arm swinging, arm swinging, arm swinging.

Walking includes but is not limited to walking backward and forward, walking in circles, and walking forward in the shape of "Zhi".

In embodiments of the invention, the functional instruction is one of the above body movements or a combination of the above body movements and does not limit the number of body movements to be performed. For example, in the embodiment of the invention, the functional instruction of the calibration sensor 103 is to tap the motion sensor 1014 three times. Three times of slapping instead of one, two or more than three times can avoid the interference caused by accidental body movements, and it is more convenient than more than three times of slapping and enhance the user experience.

In another embodiment of the present invention, the functional instruction for connecting/disconnecting a remote device (such as a handheld, mobile phone, ipad, etc.) is that the user first bends once and then twists his body twice.

In another embodiment of the invention, the functional instruction to activate the sensor 103 is to tap the motion sensor twice and press the motion sensor twice. The functional instruction to stop sensor 103 is to tap the motion sensor once and press the motion sensor three times.

Combined with the direction of the coordinate system shown in FIG. 1, in order to enrich the body movements available to users and enhance user experience, the flapping, swinging and pressing of the motion sensor 1014 in different directions can also be used to set functional instructions. In one embodiment of the invention, the functional instruction to adjust the signal intensity of the transmitter 1013 is to tap the motion sensor 1014 four times in the positive direction of the X axis to enhance the signal intensity of a first gear, and tap the motion sensor 1014 four times in the opposite direction of the X axis to reduce the signal intensity of a first gear. In another embodiment of the invention, flapping the motion sensor 1014 along the positive direction of the Y axis four times can enhance the signal strength of two levels, and flapping the motion sensor 1014 along the opposite direction of the Y axis four times can reduce the signal strength of two levels. In another embodiment of the invention, flapping the motion sensor 1014 along the positive direction of the Z axis for four times can enhance the signal strength of the three levels, and flapping the motion sensor 1014 along the opposite direction of the Z axis for four times can reduce the signal strength of the three levels.

In order to avoid the interference caused by unnecessary or wrong body movements, users need to complete the body movements corresponding to the expected instructions within a fixed time t. Here, the fixed time t can be set to any time within 0.5~5 s according to the habits of users. Preferred, t=1 s. Case, the implementation of the present invention, for example, users within 1 s flap motion sensor 1014 three times, this is a valid body movements, expecting to perform the function of the calibrated sensor 103 orders, but because of the external factors users in more than is after beating a motion sensor, 1014, this is invalid body movements, if there is no fixed time t, the combination of body movements will be recognized to adjust the transmitter 103 signal strength.

Technicians in this field can understand that the body movements or the combination of body movements corresponding to the above functional instructions are not unique. Users can set the corresponding body movements or the combination of body movements according to their own habits and conditions.

Figure 4A:
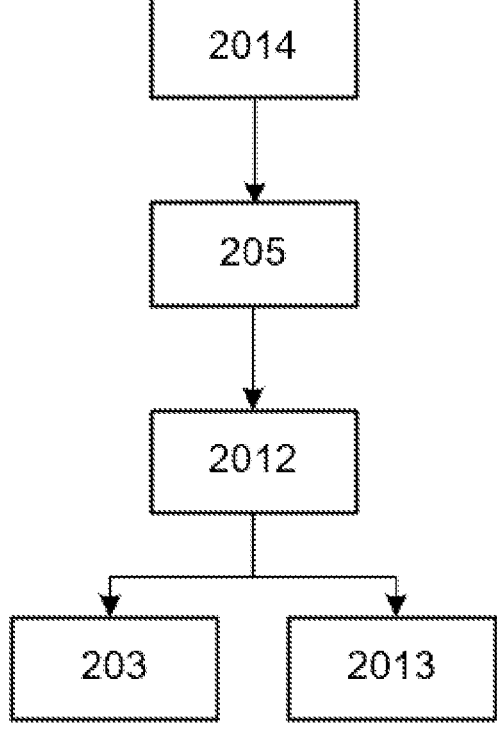
FIG. 4A-FIG. 4b is a schematic diagram of functions including action confirmation modules according to different embodiments of the invention.
Figure 4B:
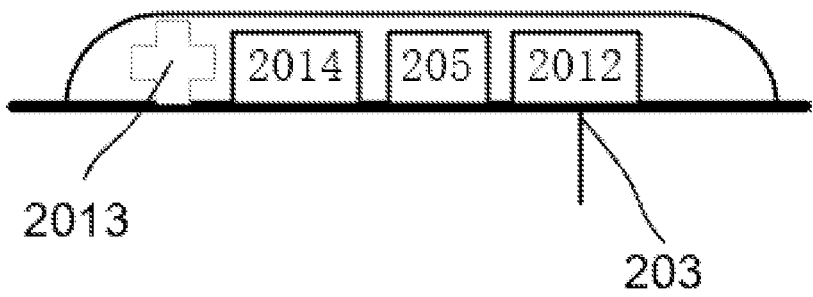

FIG. 4a-FIG. 4b is a schematic diagram of functions including action confirmation modules according to different embodiments of the invention.

The motion confirmation module 205 is connected with the motion sensor 2014 to confirm whether the user's body movements meet the requirements (such as the set speed, intensity or frequency, etc.), so as to improve the accuracy of the analyte detection system. When the motion sensor 2014 detects the user's specific body movement, but the body movement does not meet the set requirements, the analyte detection system will issue a specific form of alarm (such as light, sound, vibration, etc.), so that the user can make a more standard body movement again. Similarly, the analyte detection system can emit certain forms of cues (such as glow, sound, vibration, etc.) when the body movement is in accordance with the requirements.

The embodiment of the invention does not place specific restrictions on the position set by the motion confirmation module 205 and the connection relationship with other modules, provided that the conditions for the connection of the motion confirmation module 205 and the motion sensor 2014 can be satisfied. Preferably, in the embodiment of the invention, the action confirmation module 205 is arranged between the motion sensor 2014 and the internal circuit 2012, as shown in FIG. 4A. Therefore, when the motion sensor 2014 senses and recognizes the user's body movements, the motion confirmation module 205 confirms whether the movements meet the requirements. If it meets the requirements, the internal circuit 2012 indirectly receives the body movement instruction information from the motion sensor 2014 and controls the sensor 203 or the transmitter 2013 to execute the corresponding function instruction. At this point, there is an operational connection between the motion sensor 2014 and the internal circuit 2012.

In another embodiment of the present invention, the motion confirmation module 205 may also be connected only to the motion sensor 2014, as shown in FIG. 4b. When the motion confirmation module 205 confirms that the body movement meets the requirements, the internal circuit 2012 can directly obtain the corresponding instructions and control the sensor 203 or the transmitter 2013 to execute the corresponding functional instructions.

Among them, the principle and mode of the internal circuit 2012 to control the sensor 203 and the transmitter 2013 are referred to above, and will not be repeated here.

Figure 5:
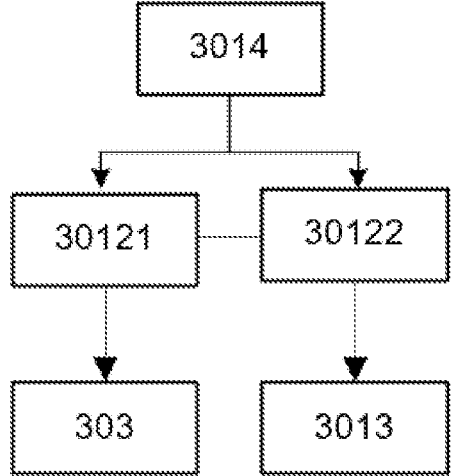
FIG. 5 is a schematic diagram of a function of a second subcircuit and a first subcircuit according to another embodiment of the invention.

FIG. 5 is a schematic diagram of a function of a second subcircuit and a first subcircuit according to another embodiment of the invention.

In the embodiment of the invention, the first subcircuit 30121 controls the sensor 303, the second subcircuit 30122 controls the transmitter 3013, and the first subcircuit 30121 is electrically connected with the second subcircuit 30122 to transmit the analyte parameter information detected by the sensor 303 to the transmitter 3013. The motion sensor 3014 is electrically connected with the first subcircuit 30121 and the second subcircuit 30122 respectively. If the body movement is the functional instruction of sensor 303, when the motion sensor 3014 senses the user's body movement, the signal generated by the motion sensor 3014 is recognized by the first subcircuit 30121, but not by the second subcircuit 30122. At the same time, the first subcircuit 30121 controls the sensor 303 to execute the corresponding functional instruction. If the body movement is about the function instruction of the transmitter 3013, when the motion sensor 3014 senses the user's body movement, the signal generated by the motion sensor 3014 is recognized by the second subcircuit 30122, but cannot be recognized by the first subcircuit 30121. At the same time, the second subcircuit 30122 controls the transmitter 3013 to execute the corresponding functional instructions. This can further improve the accuracy of the analyte detection system for body movement recognition.

In other embodiments of the invention, the first subcircuit 30121 is wirelessly connected with the second subcircuit 30122, and the motion sensor 3014 is electrically connected with the first subcircuit 30121 and the second subcircuit 30122 respectively.

In another embodiment of the invention, the first subcircuit 30121 is connected wirelessly with the second subcircuit 30122, and the motion sensor 3014 is connected wirelessly with the first subcircuit 30121 and the second subcircuit 30122 respectively.

Figure 6:
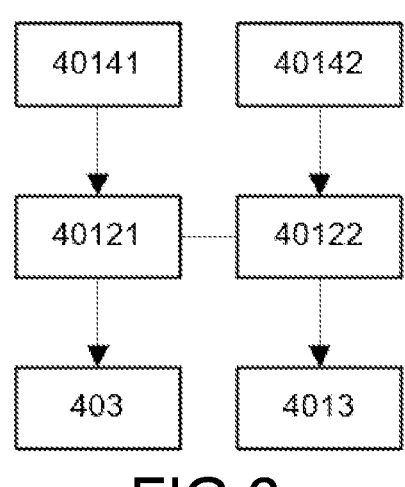
FIG. 6 is a schematic diagram of a second embodiment of the invention including a first sub-motion sensor and a second sub-motion sensor according to the invention.

FIG. 6 is a schematic diagram of a second embodiment of the invention including a first sub-motion sensor and a second sub-motion sensor according to the invention.

In the embodiment of the invention, the internal circuit 4012 includes a first subcircuit 40121 and a second subcircuit 40122. The first sub-motion sensor 40141 is connected with the sensor 403 through the first subcircuit 40121, and the second sub-motion sensor 40142 is connected with the transmitter 4013 through the second subcircuit 40122, in embodiments of the invention, the "connected with" may be either an electrical connection or a wireless connection. The first sub-motion sensor 40141 stores the body movement data corresponding to the sensor 403 function instruction, and the second sub-motion sensor 40142 stores the body movement data corresponding to the transmitter 4013 function instruction. When the user sends out the limb movement corresponding to the function instruction of the sensor 403, the first sub-motion sensor 40141 can recognize and generate the signal, which is transmitted to the first subcircuit 40121. The first subcircuit 40121 controls the sensor 403 to complete the corresponding function instruction. At this time, the second sub-motion sensor 40142 cannot recognize the limb movement. So no signal will be generated, let alone transmitted to the second subcircuit 40122. When the user sends out the limb movement corresponding to the function instruction of the transmitter 4013, the second sub-motion sensor 40142 can recognize and generate the signal, which is transmitted to the second subcircuit 40122. The second subcircuit 40122 controls the transmitter 4013 to complete the corresponding function instruction. At this time, the first sub-motion sensor 40141 cannot recognize the limb movement. So no signal will be generated, let alone transmitted to the first subcircuit 40121. In this way, the accuracy of the analyte detection system for body movement recognition can be further improved, and the power consumption of the system can also be reduced.

Figure 7A:
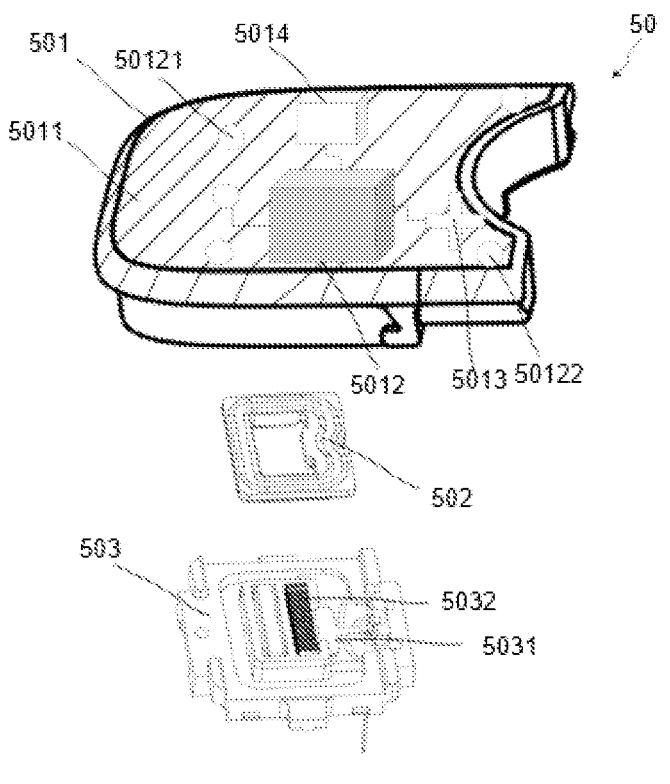
FIG. 7*a* is a structural schematic diagram of an analyte detection system according to another embodiment of the invention.
Figure 7A:
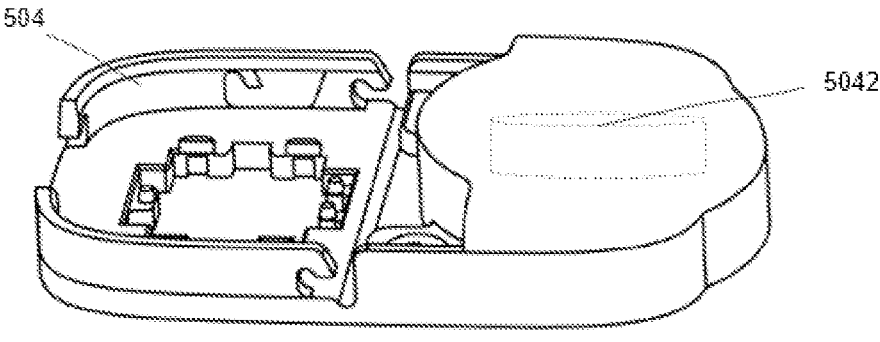
Figure 7B:
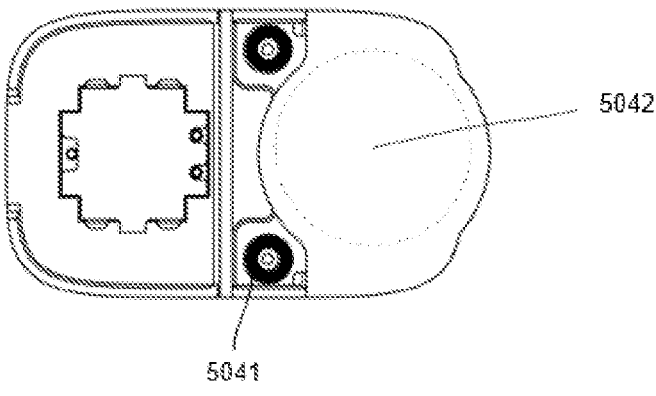
FIG. 7*b* is a structural schematic diagram of the bottom case housing of an analyte detection system according to another embodiment of the invention.

FIG. 7a is a structural schematic diagram of an analyte detection system according to another embodiment of the invention. FIG. 7b is a structural schematic diagram of the bottom case housing of an analyte detection system according to another embodiment of the invention. Analyte detection system 50 includes transmitter unit 501, transmitter unit 501 includes transmitter shell 5011, internal circuit 5012, transmitter 5013 and motion sensor 5014. Internal circuit 5012, transmitter 5013 and motion sensor 5014 are arranged inside the transmitter shell 5011. In the embodiment of the invention, the internal circuit 5012 includes the first electrical contact 50121 leading to the outer part of the transmitter shell 5011, and the area in contact with the first electrical contact 50121 and the transmitter shell 5011 is laid with waterproof and insulating materials, preferably including but not limited to one or more combinations of flexible materials, elastic materials and malleable materials. Further preferred, including but not limited to one or more combinations of epoxy resins, silicone resins, and gels.

In the embodiment of the invention, the transmitter 5013 is used to transmit information with the outside world, which includes but is not limited to one or more combinations of Bluetooth, NFC, RFID, Li-Fi and WIFI. The information transmission objects are users' hand-held computers, mobile phones, tablets, etc., so that users can understand the parameter information of the analyte in a visual form, which is convenient for users to use.

In the embodiment of the invention, the motion sensor 5014 includes but is not limited to one or more of the acceleration sensor, tilt sensor, vibration sensor and rotation sensor.

In the embodiment of the invention, the motion sensor 5014 is a three-axis acceleration sensor, which can detect the change of acceleration in X, Y and Z axis directions, and has the advantage of rapid detection of body movements, more comprehensive recognition of body movements, and improved sensitivity of movement detection.

In another embodiment of the invention, the motion sensor 5014 is a rotation sensor, which can accurately detect the user's rotation and other body movements, such as turning in a circle, etc.

In another embodiment of the invention, the motion sensor 5014 is a vibration sensor, and the vibration sensor can accurately detect the user's flapping and other body movements.

In another embodiment of the invention, the motion sensor 5014 is a combination of a three-axis acceleration sensor, a rotation sensor and a vibration sensor. The combined motion sensor can realize more and more accurate detection of body movements, enrich the choice of the user and improve the user experience.

Continuing with FIGS. 7a and 7b, the analyte detection system 50 also includes a seal ring 502 to provide waterproof protection in wet or underwater environments. Sensor 503 includes sensor 5031 and conductive tape 5032. The sensor 5031 is connected with the conductive tape 5032. The sensor 5031 is used to pierce the human skin to detect the parameter information of the analyte. Can also be a blood protein, dopamine, epinephrine, thyroid hormones may be exist in human body fluids such as chemicals, sensor 5031 was detected in human body fluids of the analyte, the electrodes (not shown in the figure out) and membrane system (not shown in the figure out) on the sensor 5031 will react according to the kinds and concentrations of analyte and, in turn, produce different forms of electrical signals. The electrical signal can be used to indicate the analyte parameter information. The electrical signal generated on the sensor 5031 is transmitted to the internal circuit 5012 through the conductive tape 5032 and the first electrical contact 50121. After signal processing, such as denoising, amplification and waveform sorting, etc., of the internal circuit 5012. The analyzer parameter information is transmitted to the outside world by the transmitter 5013, that is, the transmitter 5013 is electrically connected with the internal circuit 5012. The bottom case housing 504 is used to assemble the transmitter unit 501, sealing ring 502 and sensor 503 and fix them on the surface of human skin. The bottom case housing 504 also includes at least two second electrical contacts 5041, which are respectively connected to the positive and negative electrodes of the battery 5042. The internal circuit 5012 also includes a third electric contact 50122, which is led to the outside of the transmitter shell and corresponding to the second electric contact 5041. The third electric contact 50122 is electrically connected with the second electric contact 5041, so that the battery 5042 provides electric energy for the transmitter unit 501. Battery 5042, sealed in bottom case housing 504, is used to provide electric energy for transmitter unit 501. Since bottom case housing 504 will be discarded when sensor 503 is used up, the user will replace the battery when bottom case housing 504 is replaced. The battery can maintain high performance state to provide electric energy for transmitter unit 501, so as to ensure the detection reliability of analyte detection system 50.

In the embodiment of the invention, the steps of indicating the sensor 503 and transmitter 5013 function instructions according to the user's body movements are consistent with the foregoing, and will not be repeated here.

Figure 8:
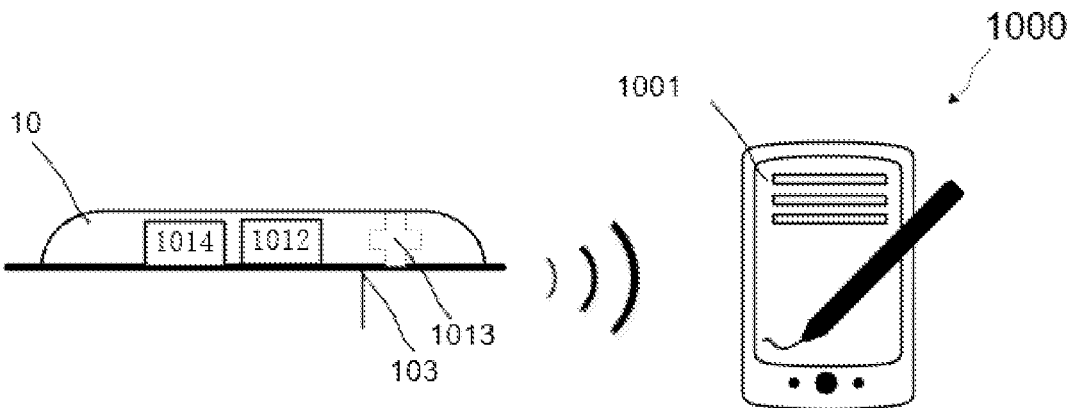
FIG. 8 is a structural schematic diagram of a continuous glucose monitoring device for an embodiment of the invention.

FIG. 8 is a structural schematic diagram of a continuous glucose monitoring device for an embodiment of the invention. The continuous glucose monitoring device 1000 comprises an analyte detection system 10 and a receiver 1001. The transmitter 1013 of the analyte detection system 10 transmits the analyte parameter information detected by sensor 103 to the outside world, which is received by the receiver 1001, and indicates the analyte parameter information to the user in a visual way. Receiver 1001 includes but is not limited to handheld, mobile phone, tablet and other devices. The mode of information transmission between transmitter 1013 and receiver 1001 includes but is not limited to one or more combinations of Bluetooth, NFC, radio frequency identification (RFID), Light Fidelity (Li-Fi), and Wireless Fidelity (WIFI).

To sum up, the embodiment of the invention discloses an analyte detection system. After the user's body movement is sensed by the motion sensor as a function instruction, the internal circuit can directly control the sensor or transmitter to execute the function instruction, without the user manually entering the function instruction, so as to improve the user's experience.

Although some specific embodiments of the invention have been detailed through examples, technicians in the field should understand that the above examples are for illustrative purposes only and are not intended to limit the scope of the invention. Persons skilled in the field should understand that the above embodiments may be modified without departing from the scope and spirit of the present invention. The scope of the invention is limited by the attached claims.

The invention claimed is:

1. An analyte detection system, comprising:
a bottom case housing adapted to be installed on a surface of human skin;
a sensor, assembled on the bottom case housing, wherein the sensor comprises an analyte detection sensor and a conductive tape, the analyte detection sensor is used for piercing the human skin to detect analyte parameter information, the conductive tape is formed alternately by a conductive area and an insulation area;
a transmitter unit, including a transmitter shell, an internal circuit, a transmitter and a motion sensor, wherein the internal circuit is set within the transmitter shell, the internal circuit at least includes a first electrical contact which led out to outside of the transmitter shell, which is in electrical contact with the conductive tape to obtain the analyte parameter information, the transmitter is adapted to transmit the analyte parameter information to outside world, the motion sensor and the internal circuit are operationally connected, the motion sensor senses or recognizes body movements according to the motion sensor sensing or recognizing the body movements, the internal circuit controls the sensor or the transmitter to execute functional instructions; and
a battery for supplying electrical energy to the transmitter unit,
wherein the internal circuit controls the sensor or the transmitter to execute the corresponding functional instruction according to a sequence of at least two repetitions of the body movements and/or a combination of the body movements,
wherein the functional instructions include at least one of sensor calibration, sensor activation or stop, adjustment of blood glucose concentration alarm threshold, adjustment of signal strength, and connection/disconnection of remote devices.

2. Analyte detection system of claim 1, wherein the battery is sealed in the transmitter shell to provide electric energy for the transmitter unit.

3. Analyte detection system of claim 1, wherein the battery is sealed in the bottom case housing, the bottom case housing comprises at least two second electrical contacts, respectively connected to positive and negative poles of the battery, the internal circuit also includes a third electrical contact leading to an outer part of the transmitter shell and corresponding to the second electrical contact, the third electrical contact is electrically connected with the second electrical contact, so that the battery provides electrical energy to the transmitter unit.

4. Analyte detection system of claim 1, wherein the internal circuit also includes a first subcircuit connected with the sensor and a second subcircuit connected with the transmitter, and the first subcircuit and the second subcircuit are electrically connected.

5. Analyte detection system of claim 4, wherein the motion sensor is connected with the first subcircuit and the second subcircuit.

6. Analyte detection system of claim 4, wherein the motion sensor comprises a first sub-motion sensor and a second sub-motion sensor, the first subcircuit and the first sub-motion sensor are electrically connected, the second subcircuit and the second sub-motion sensor are electrically connected, the first subcircuit and the second subcircuit are electrically connected, the first sub-motion sensor recognizes the body movements corresponding to a function instruction of the sensor, the second sub-motion sensor recognizes the body movements corresponding to a function instruction of the transmitter.

7. Analyte detection system of claim 1, wherein the body movements include at least one of walking, jumping, running, squatting, leg movements, arm movements, bending, body twisting and/or flapping, swinging and pressing on the motion sensor.

8. Analyte detection system of claim 1, wherein the body movements sensed or recognized by the motion sensor within a fixed time t are effective body movements, and the body movements sensed or recognized outside a fixed time t are invalid body movements, according to the effective body movements, the internal circuit controls the sensor or transmitter to execute corresponding functional instructions.

9. Analyte detection system of claim 8, wherein the fixed time t is 0.5 s~5 s.

10. Analyte detection system of claim 8, wherein the fixed time t=1 s.

11. Analyte detection system of claim 1, wherein the motion sensor is one or more of an acceleration sensor, an inclination sensor, a vibration sensor and a rotation sensor.

12. Analyte detection system of claim 11, wherein the acceleration sensor is a three-axis acceleration sensor.

13. Analyte detection system of claim 1, further comprising a body motion confirmation module, which is connected with the motion sensor and is adapted to confirm whether the user's body movements meet requirements.

14. A continuous glucose monitoring device, comprising an analyte detection system as described in claim 1 and a receiver, the receiver is used for receiving the analyte parameter information transmitted by the transmitter and indicating the analyte parameter information to user.

* * * * *